United States Patent
Fegan, Jr.

[11] Patent Number: 6,051,126
[45] Date of Patent: Apr. 18, 2000

[54] METHOD FOR ANALYZING PRECIOUS METALS

[76] Inventor: Lloyd V. Fegan, Jr., 1173 Meadowbrook Cir. West, Allentown, Pa. 18103

[21] Appl. No.: 09/280,275

[22] Filed: Mar. 29, 1999

Related U.S. Application Data

[62] Division of application No. 08/811,874, Mar. 5, 1997, Pat. No. 5,888,362, which is a continuation of application No. 08/346,616, Nov. 30, 1994, abandoned.

[51] Int. Cl.$^7$ .................................................... G01N 27/26
[52] U.S. Cl. .......................... 205/790; 204/400; 205/775; 401/198
[58] Field of Search ..................... 204/400, 434, 204/435; 205/775, 790, 791, 791.5; 401/198, 199

[56] References Cited

U.S. PATENT DOCUMENTS

| | | | |
|---|---|---|---|
| 2,531,747 | 11/1950 | Stearn | 204/434 |
| 2,939,827 | 6/1960 | Jacobson et al. | 204/432 |
| 3,575,834 | 4/1971 | Hoole et al. | 204/435 |
| 4,006,063 | 2/1977 | Ensanian | 205/791.5 |
| 4,269,526 | 5/1981 | Dupre | 401/198 |
| 4,453,849 | 6/1984 | Fernandez | 401/198 |
| 5,480,250 | 1/1996 | Birden | 401/199 |

*Primary Examiner*—T. Tung
*Attorney, Agent, or Firm*—Charles A. Wilkinson

[57] ABSTRACT

The nature of a metal sample, such as the purity of precious metals and metal alloys, such as gold, is determined using a handheld probe having an electrode embedded in an electrolyte in a reservoir of the probe and arranged to conduct electrically with the sample through the electrolyte and a fibrous tip. The tip can resemble the point of a marker or writing instrument. The tip is in fluid communication with the reservoir containing the electrolyte, and preferably has the electrode embedded therein. An electrical connection with the electrode is made at the rear of the probe. For testing gold purity, the electrode is preferably a thin platinum wire extending through the reservoir and into the tip to just behind the tip surface. A battery is coupled to a calibration potentiometer whereby the voltage on a millivoltmeter is set to full scale when the probe is open circuited. When coupled to the sample in a circuit, the galvanic cell formed by the same, the electrode and the electrolyte reduces the voltage sensed at the meter, as a function of the extent of galvanic action. Preferably the electrolyte is a weak acid including nitric acid and ammonium chloride salt in aqueous solution.

11 Claims, 5 Drawing Sheets

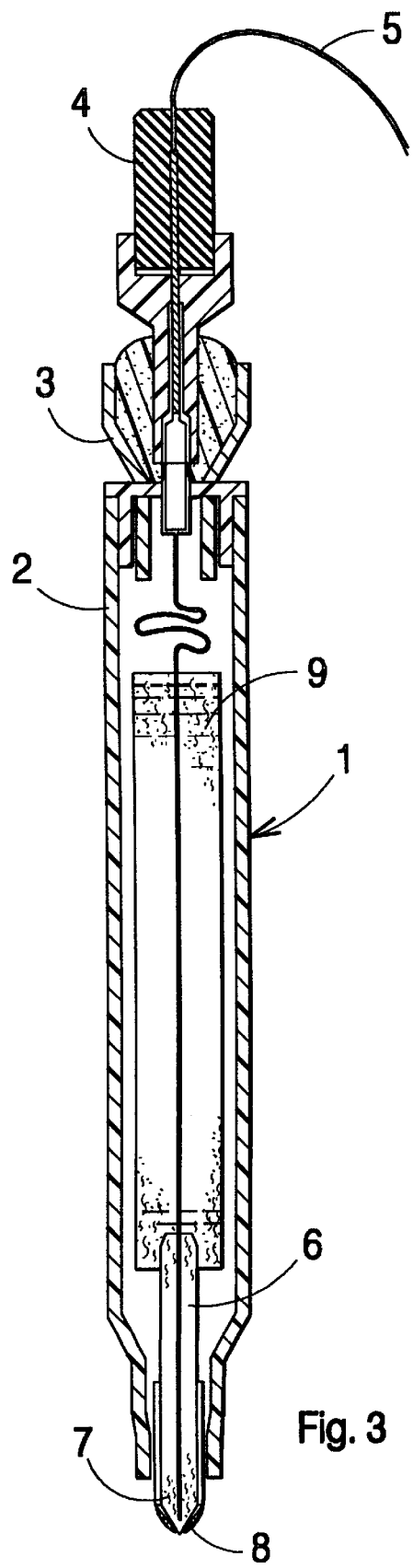
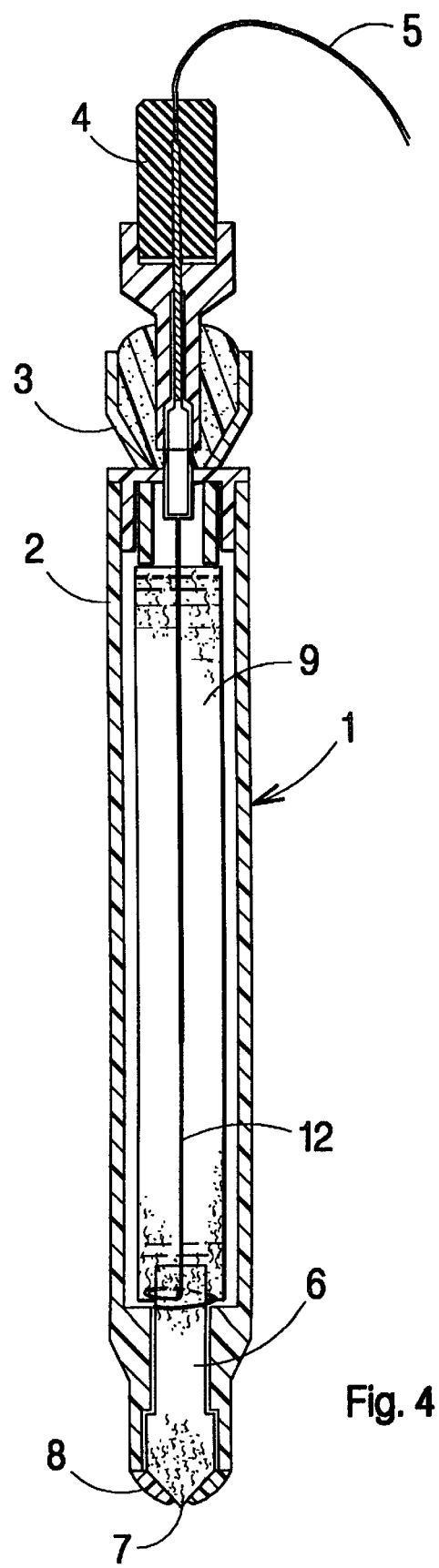
Fig. 3
Fig. 4

METHOD FOR ANALYZING PRECIOUS METALS

RELATED APPLICATIONS

This application is a division of U.S. application Ser. No. 08/811,874 filed Mar. 5, 1997, now U.S. Pat. No. 5,888,362, which was a continuation of U.S. application Ser. No. 08/346,616 filed Nov. 30, 1994, now abandoned.

BACKGROUND OF THE INVENTION

1. Field of the Invention

The invention relates to apparatus and methods for assay of metals, especially for assessing the purity of precious metals and alloys. A meter circuit coupled to an inventive probe measures the extent of galvanic action of dissimilar metals in the presence of an electrolyte, one of the metals being the sample to be assayed. The invention is useful for testing the metal content of coins, art objects jewelry, and the like, in that the probe can simply be touched against the sample to provide a reading. The reading is developed by measuring the extent to which a biasing voltage is reduced by galvanic action between the sample and a preferably platinum probe conductor embedded in a fibrous absorbent medium containing an electrolyte.

2. Prior Art

There are a number of analytical techniques used to assess the nature of metal samples, for example to determine the precious metal content of coins, art objects and items of jewelry. A traditional test used by jewelers and precious metals traders to determine the purity of gold alloys, for example, relies on a set of "gold pencils" that are used in comparing the results of a scratch test. In this method, the jeweler has a number gold alloy "pencils" or rods used as references. The gold alloy pencils can be graduated, for example, over a range of 4 to 24 karat gold alloy compositions.

The reference gold alloy pencils are used to mark an abrasive stone or touchstone, for comparison with a mark made using the sample. The jeweler makes a small scratch using the specimen to be analyzed, and reference scratches with the gold alloy rods or pencils, in each case leaving a trace quantity of metal. The jeweler then places an acid such as nitric acid or aqua regia (an aqueous solution of hydrochloric and nitric acids) on the abrasive stone and compares the color of the traces produced by the specimen scratch with the color of the traces of the several gold alloy rod scratches, to assess the karat value of the sample.

An experienced jeweler can estimate the amount of gold in karats in the specimen being analyzed by comparing the colors of the sample trace and reference traces. This method, which is still widely used, is dependent on the skill and experience of the jeweler employing the test. Such testing is time consuming and causes some damage to the sample. Moreover, the results can turn on subjective judgment. Errors made in technique or in judgment in this field, however, can be costly, either to the customer or to the jeweler.

More recently, attempts have been made to develop a more objective assaying technique using electrical testing apparatus.

One technique is to measure the electromotive force (EMF) developed as a result of galvanic action when the specimen to be analyzed is brought into conductive contact with a dissimilar metal. This is accomplished in the presence of an electrolyte The sample and the dissimilar metal electrode produce a galvanic voltage in the manner of a very low power battery, which can be measured to assess the nature of the sample. Several of these prior apparatus and methods are described in the following U.S. Pat. Nos.:

| | | |
|---|---|---|
| No. 2,531,747 | Stearn | 1950 |
| U.S. Pat. No. 3,282,804 | Stearn | 1966 |
| U.S. Pat. No. 4,376,027 | Smith | 1983 |
| U.S. Pat. No. 4,799,999 | Medvinsky | 1989 |
| U.S. Pat. No. 5,080,766 | Moment | 1992 |
| U.S. Pat. No. 5,218,303 | Medvinsky | 1993 |

Whereas the electromotive force produced is relatively small and the differences in electromotive force to be measured between nearly comparable samples is even smaller (e.g., 20 karat vs. 22 karat gold), the accuracy of measurement turns on the precise manner in which the sample, electrolyte and electrode come into contact and interact. Insofar as the apparatus and methods described in these prior patents require the judgment and skill of an experienced user for setup and use, they could advantageously be improved. Furthermore, it would be advantageous to provide an objective form of test that is more convenient, does not stain or damage the specimen, and produces accurate results repeatably and reliably without a great deal of setup and adjustment.

The commercially available apparatus of the type described in U.S. Pat. Nos. 4,799,999 and 5,218,303 to Medvinsky are such that a quantity of electrolyte is applied to the sample for each test, for example being discharged from a syringe-like means. An electrode is brought into contact with the electrolyte and into proximity with the sample, without shorting directly against the sample, thereby making a so-called "wet junction." A gelatinous or viscous electrolyte or an electrolyte paste can be used. In other arrangements, the sample is dipped into a container of electrolyte.

When coupled into a circuit, galvanization anodizes the sample. As a result these procedures can leave a stain on the specimen. A stain of this type typically must be removed from the specimen after the test, for example with an abrasive that removes specimen material in a manner not unlike the use of a touchstone. In addition, such apparatus is not convenient for allowing tests to be performed quickly on several specimens in rapid succession, because a fresh supply of the gel or paste electrolyte must be dispensed for each test.

The voltage reading obtained using the test can be affected by the availability of free ions in the electrolyte and other factors. According to Medvinsky, an exciting voltage is applied to the galvanic circuit including the specimen for five seconds and then released, and the decaying galvanic voltage is measured after a predetermined time (e.g., five more seconds). Each test thus requires at least ten seconds and the accuracy of the results is dependent on timing. The galvanic potential achieved and the decay rate must be measured accurately. The results are compared to standards stored in the memory of the electronic apparatus or manually by comparison with tables developed by testing reference samples of known purity.

For repeatable results in galvanic testing, the test conditions must be identical from test to test. Thus the surfaces of the specimen(s) and the electrode, and their interaction with the electrolyte, cannot be materially different. This is difficult to achieve. The electrode tip of the prior commercial apparatus described in U.S. Pat. Nos. 4,799,999 and 5,218, 303 requires frequent cleaning to remove dried and/or spent electrolyte paste from the tip. The electrolyte gel or paste, which comprises hydrochloric acid, can dry out between tests, which affects the repeatability of results. The electrolyte also can become too liquefied and flow out of the dispenser, which can be avoided if the electrolyte is refrigerated. It would be advantageous if an electrolyte could be deployed in a more convenient manner, while still obtaining accurate and repeatable results.

Other apparatus are similarly inconvenient. For example, the technique described in U.S. Pat. No. 5,080,766—Moment requires that the entire specimen be immersed in a container filled with electrolyte. This test also requires considerable waiting time to obtain a measurement of the galvanic electromotive forces being developed.

Further problems relate to the specific circuitry used to measure the galvanic action, and typically to provide a reference voltage level that is coupled to the galvanic circuit. It is desirable to obtain a reasonable measurement span in order to obtain good resolution, ideally to distinguish down to a karat or fraction of a karat. This is also difficult to achieve, particularly at high karat levels, because the slope of a curve of galvanic action vs. karat level or purity, drops off at higher karat levels.

SUMMARY OF THE INVENTION

It is therefore an object of this invention to provide apparatus and method for making objective analyses of the composition of metals, in particular precious metal alloys, that is reliable, accurate and simple to use.

It is a further object of this invention to provide apparatus and method for analyzing the composition of precious metal alloys that can be used quickly and easily for a number of tests on a number of specimens in rapid succession.

It is a still further object of this invention to provide apparatus and method for analyzing the composition of a number of precious metal alloys, such as gold, silver, platinum, and palladium alloys that produces minimal damage or staining of the specimen.

It is another object of this invention to provide a apparatus for analyzing the composition of precious metal alloys that provides a direct, easily understood reading to the user.

It is a further object of the invention to provide an improved electrode and electrolyte handling technique for a galvanic analyzer, that overcomes the inconvenience and variability of known devices.

These and other objects are attained according to the invention in a hand held probe for analyzing a test specimen, especially for precious metal content, comprising a tubular reservoir containing an electrode in an electrolyte, such as hydrochloric acid or aqua regia, but also possibly a noncorrosive electrolyte such as ammonium chloride for providing free ions. The probe has an absorbent, nonconductive, acid resistant fiber tip at the front end of the probe, the tip carrying the electrolyte and enclosing the metal electrode, namely a thin platinum electrode having one end extending into the fiber tip and the other end extending into the acidic electrolyte in the reservoir. A first electrical connection at the rear end of the probe is electrically connected to a test circuit having a substantially constant voltage source such as a battery, and a meter for measuring the EMF developed between the electrode and the sample. A second electrical connection is made with the sample directly, for example with a touch probe or alligator clip. The EMF generated by galvanic reaction between the platinum electrode and that portion of the test specimen contacted by the electrolyte-saturated fiber tip is subtracted from the substantially constant EMF from the battery to produce a voltage signal that can be compared to reference values for determining the nature of the specimen. For measuring precious metal content such as the purity of gold, the signal developed varies with the precious metal content of the test specimen.

BRIEF DESCRIPTION OF THE DRAWINGS

FIG. 3 is a partial section view of an alternative probe embodiment.

FIG. 4 is a partial section view showing another alternative probe embodiment.

DESCRIPTION OF THE PREFERRED EMBODIMENTS

In general, the apparatus and method of this invention for analyzing a test specimen for gold content or other precious metal content is based on developing and measuring an electromotive force (EMF) due to electrical conduction between two dissimilar metals or metal alloys, namely an electrode and the sample to be analyzed. U.S. Pat. Nos. 2,531,747 and 3,282,804 to Stearn generally describe this type of analytical technique for analyzing metal alloys, and the patents are hereby incorporated. The galvanic voltage results from the difference in availability of electrons in the different metals or alloys, and provides a net current when the metals or alloys are coupled through an electrolyte.

The galvanic voltage generated by the dissimilar metals or metal alloys is generated using the touch probe of the invention, and is measured by subtracting the galvanic EMF from that of a battery or similar reference level at a constant reverse polarity voltage. The test circuit is adjusted to provide a full scale reading and the net galvanic output voltage measured as percentage of full scale. The measurement is roughly proportional to the gold or other precious metal content of the test specimen and provides a means by which the purity of the sample can be tested. This technique is potentially useful to determine the nature of the metal in the sample, but is primarily useful for determining the purity of precious metals such as gold.

Figures 1, 2:
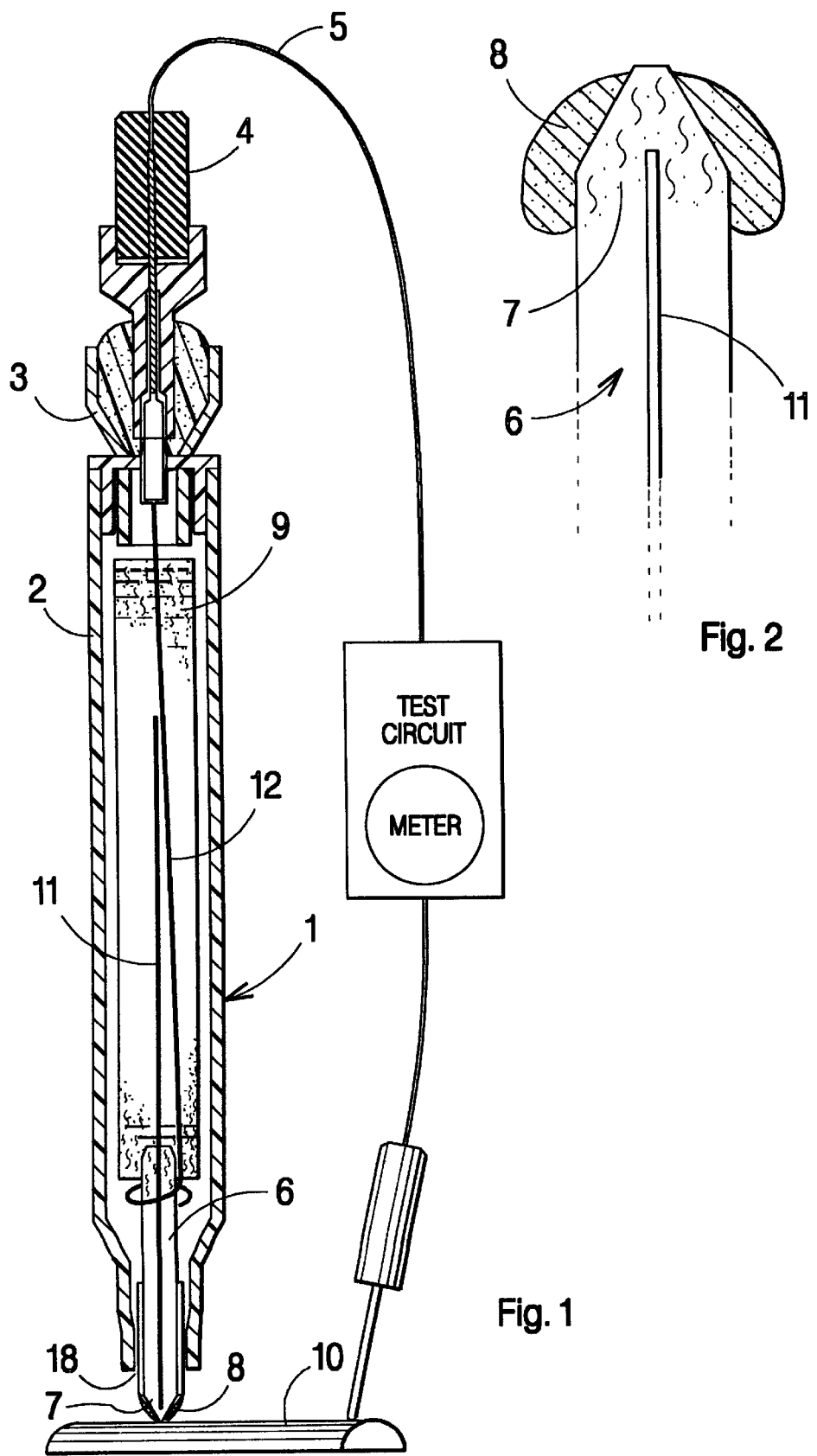
FIG. 1 is a cross-sectional view of a hand-held test probe according to a first embodiment of the invention.
FIG. 2 is an enlarged view of the tip of front end of the hand-held test probe of FIG. 1.

It is an aspect of the invention that such a measurement is made using an improved form of electrode probe. FIG. 1 is a cross-sectional view of a first embodiment of the hand-held test probe of the invention. Probe 1 generally comprises a cylindrical body 2 made of plastic or other substantially electrically non-conductive material. A top cap 3 on the probe 1 is fitted with a jack 4 to enable electrical connection of the probe to a lead or wire 5 coupled to the electrical circuitry for providing the reference voltage and making the EMF measurement. The electrical connection can be made via a miniature phone jack and plug as shown.

The end of probe 1 to be touched against the sample is fitted with an absorbent, non-conductive, acid resistant synthetic compressed fiber tip 6. The tip is advantageously of the type used in fiber tipped markers, highlighters and the like, namely including a nonwoven batt of synthetic fibers. The fiber tip 6 is preferably formed with a truncated conical or tapered flat end 7, the sides of which are coated with a non-conductive epoxy resin 8, as best illustrated in the enlarged view in FIG. 2. The epoxy resin serves several purposes. It reduces frictional wear on the end 7, prevents the evaporation or leakage of electrolyte from the fiber tip 6 and defines a small, specific and repeatable area of actual contact between the fiber tip 6 and the specimen 10 being tested.

The electrolyte is carried in the fibers of the tip by capillary action, and forms a path for electrical conduction between the probe and the sample. The mobility of the electrolyte in the tip can be improved by forming the nonwoven fiber batt using substantially aligned fibers, for example extending substantially parallel to the longitudinal axis of the probe. The electrolyte can be a liquid acid solution as known in conventional galvanic testing techniques, but is stored and deployed according to the invention in the particular probe arrangement as shown. Aqueous solutions including one or more of hydrochloric acid (HCl), nitric acid ($HNO_3$) and ammonium chloride ($NH_4Cl$) are possible, in each case dissociating in water to provide free ions for the galvanic reaction.

The rear end of the fiber tip 6 extends into a plastic or glass reservoir 9 contained in the interior of the probe body 2. The reservoir 9 contains the liquid acid solution that is fed to the tip of the probe and serves as an electrolyte during the testing of the test specimen 10, shown in FIG. 1.

The fiber tip 6 is provided with a thin platinum wire 11 (e.g., about 0.45 mm diameter) that preferably is embedded in the fiber tip 6 and extends into the reservoir 9. In FIG. 1, a second thin platinum connecting wire 12 couples the platinum wire 11 to the jack 4 in the top cap 3 of the probe 1. A thin plastic monofilament line or a thin plastic tube 18 is positioned between the outer periphery of the fiber tip 6 and the inner wall of the body 2 of the probe 1 and serves as an atmospheric vent to the reservoir 9.

The platinum wire or electrode can be arranged and coupled to the electrical connecting lead 5 in a number of ways, and examples are shown in FIGS. 1–4, with the same reference numbers identifying the same elements throughout the drawings. In FIGS. 1 and 2, the electrode wire extends through the body of tip 6 and into reservoir 9. A second platinum wire extends from connecting lead 5 downwardly into the reservoir, residing adjacent the wire from the tip. This arrangement allows the tip and associated wire to be inserted into the probe, but does not have a direct electrical connection along the two platinum wires. Electrical connection is achieved through the free ions of the electrolyte in reservoir 9.

In FIG. 3, the platinum wire in the probe connects directly through to the connecting jack 4. When attaching the female part of the jack (i.e., when pushing the jack into the end of the barrel), some slack is introduced, but the connection is direct. This arrangement has the advantage that the electrical resistance of the probe is less because the conductive path is mostly through conductive wire rather than through the electrolyte. A minimal electrical resistance is preferable because this resistance is in series with the test circuit and tends to reduce sensitivity.

Figure 5A:
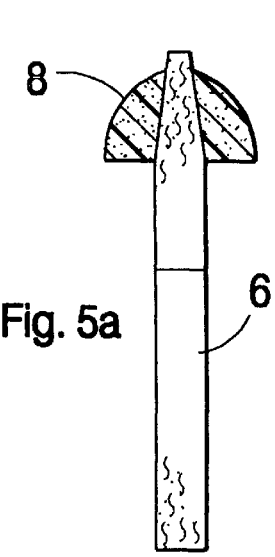
FIGS. 5a and 5b are section views showing a preferred fiber tip for use in the probe.
Figure 5B:
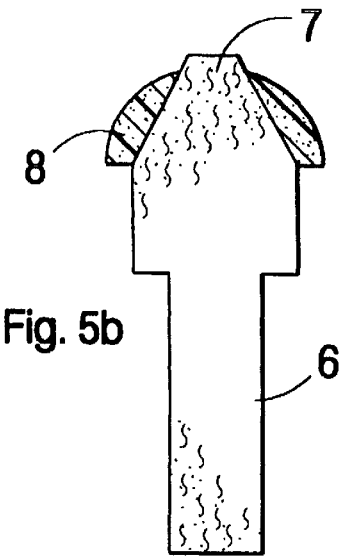

In each case, the electrode extends into the electrolyte in reservoir 9, and in FIGS. 1–3 the electrode extends nearly to the exposed end of the tip. However, as shown in FIG. 4, the electrode can also be contained fully in the reservoir portion, with a longer gap between the distal end of the electrode wire and the end of the tip. In this case, the electrical connection to the sample is also made through the tip by the electrolyte. The embodiment of FIG. 4 is more readily assembled in that attention is not required to position a wire protruding from the tip as in FIGS. 1–3. The tip can be a flattened fibrous tip of the type used for highlighters and markers, as shown in FIGS. 5a and 5b, preferably including the epoxy protective portion 8, leaving only a small area of 1–2 mm width, for touching to the specimen.

The reservoir 9 preferably comprises an acid resistant absorbent fiber mass, saturated with the liquid electrolyte The probe is sized and shaped to fit comfortably in the user's hand, for example comprising a cylindrical shape of about 15 cm in length and 1.75 cm in diameter in the area of reservoir 9.

The invention is applicable to testing of metals generally, and is particularly apt for testing specimens 10 of gold alloys to determine their purity. For testing specimens of between 4 and 18 karat gold content, for example, reservoir 9 is filled with an electrolyte, for example a solution of about 6% hydrochloric acid, the remainder being distilled water. For testing of test specimens 10 of gold alloys above 18 karat gold content and for testing platinum, palladium and silver, reservoir 9 can be filled with a solution of about 3% nitric acid, 5% hydrochloric acid and 4% ammonium chloride, the remainder being distilled water. The reservoir 9 can be a prefilled cartridge that is disposed of when empty. Another preferred electrolyte solution is 12% ammonium chloride and 1% nitric acid.

The adsorbent, non-conductive, acid resistant fiber tip 6 of the probe 1 always holds a small amount of the acidic electrolyte from the reservoir 9, which wets a small area of the specimen and provides the galvanic contact between the platinum cathode wire 11 and the test specimen 10 (see FIG. 2). There is no need to immerse the specimen 10 in a container filled with an electrolyte or to cover a large portion of the specimen with an acidic paste or gel, as required in known devices.

Figure 6:
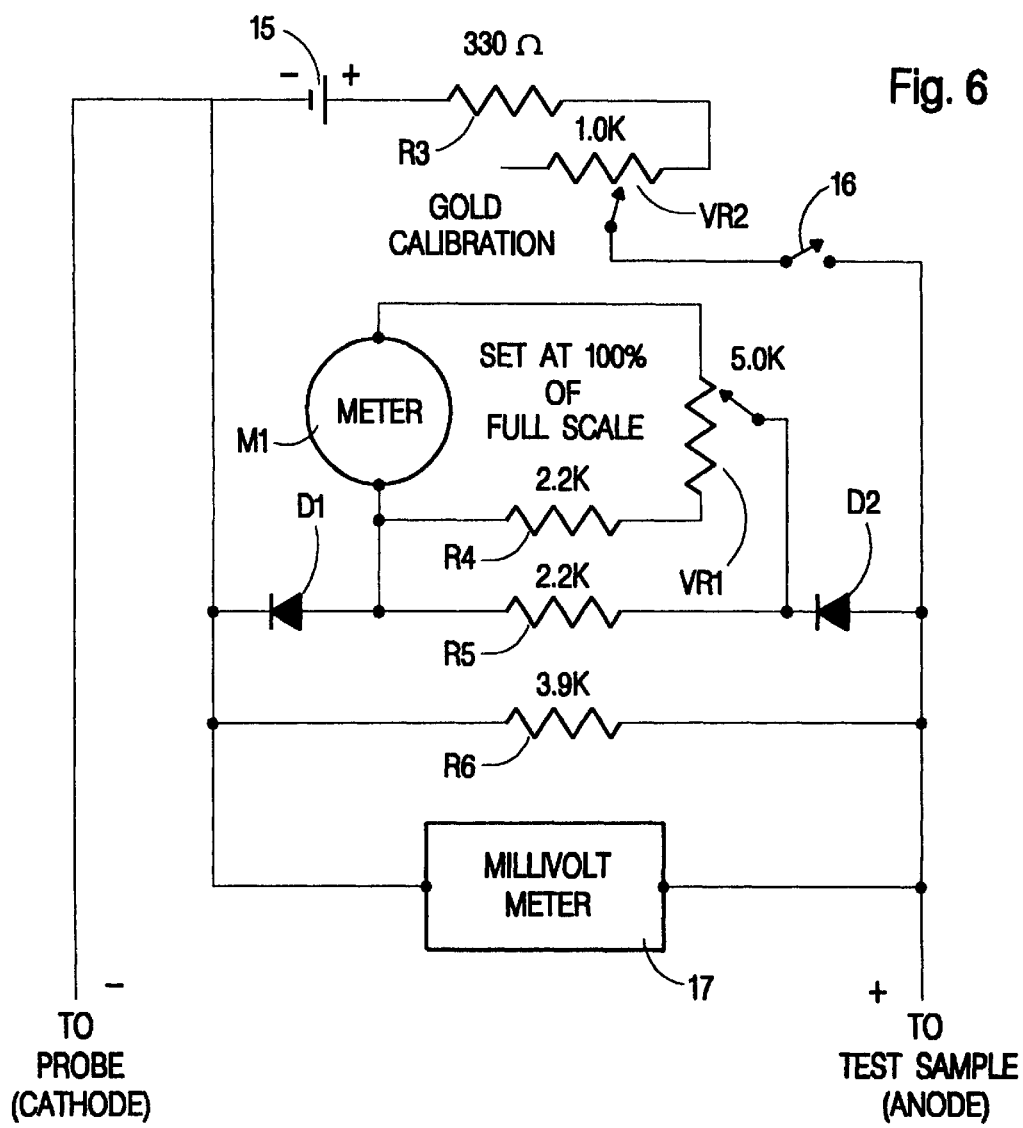
FIG. 6 is a schematic circuit diagram of a first test circuit useful with the foregoing probes.

As shown in the circuit diagram of FIG. 6, the probe 1, and in particular the thin platinum wire 11 imbedded in the fiber tip 6, serves as the cathode. The test specimen 10 serves as the anode (see FIG. 2). During the testing procedure the specimen is connected on the anode or more-positive side to wire 5' by an alligator clip or other suitable electrical connecting device. The object is to measure precisely the electromotive force developed by galvanic action between the dissimilar metals of the sample and the platinum wire contained in the probe, e.g., extending to within a short distance from the extreme end of the tip (e.g., 3 mm), or at least extending into proximity with the tip. This is accomplished by calibrating the tester to predetermined voltage conditions, touching the probe to the sample, and measuring the change from the predetermined conditions indicative of the galvanic action.

Figure 8:
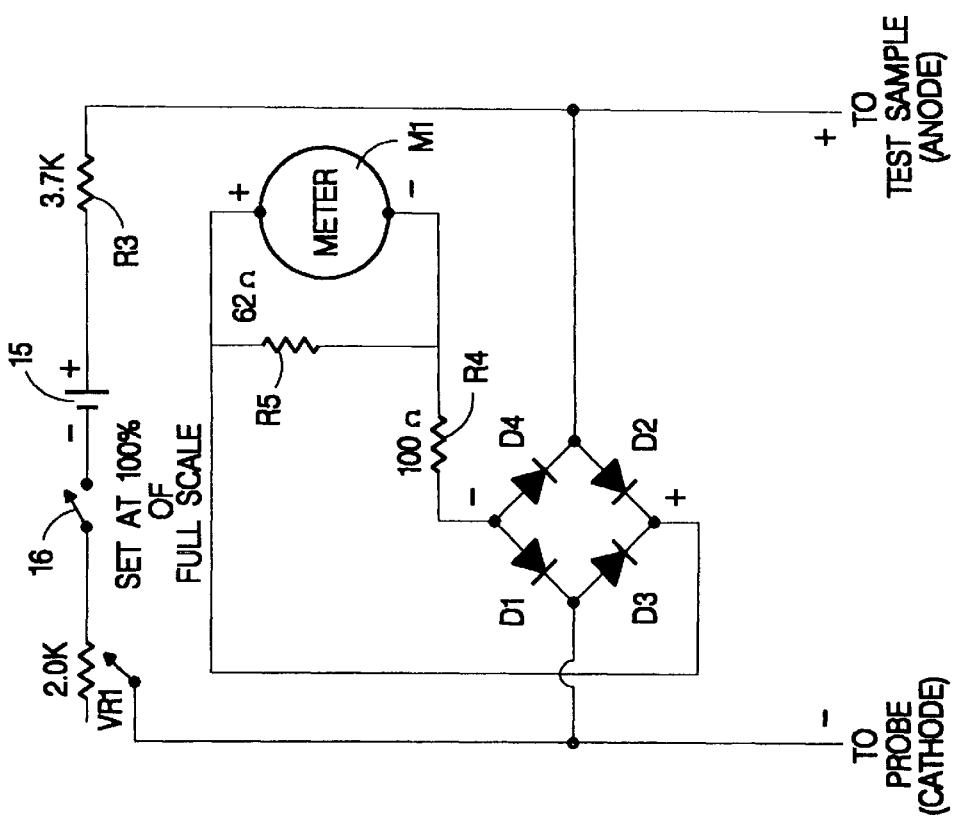
FIGS. 7 and 8 are schematic diagrams showing two alternative circuits.
Figure 7:
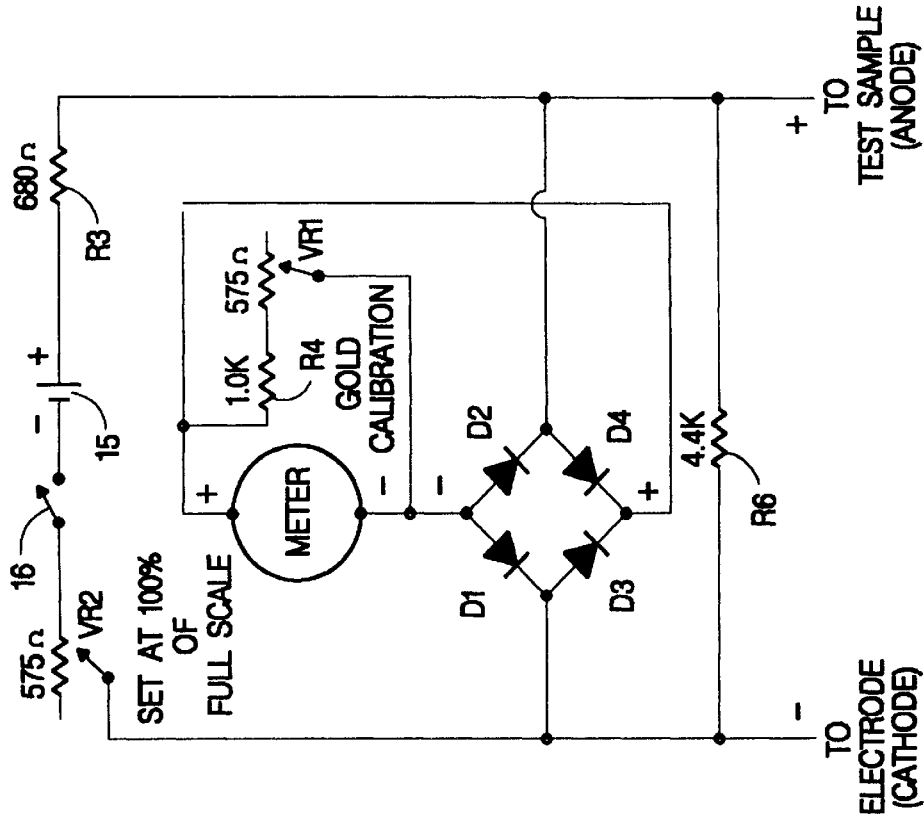

Three embodiments for the circuit used with the probe are shown schematically in FIGS. 6–8, and show some variations that are possible according to the invention. In each case, the circuits are battery powered and include adjustment means for setting the series resistance coupled between the battery and the sample, and adjustment means associated with a volt meter whereby the sensitivity of the circuit is maximized by preliminarily setting the meter to read 100% of full scale. The galvanic action produced by the sample and electrode is measured as the extent to which the meter reading is reduced when the sample is coupled into the circuit.

The same reference numbers identify circuit elements that correspond in the drawings. In FIG. 6, 1.5 volt AA battery 15 is connected to apply a voltage to the sample, via a switch 16, a series fixed resistor R3 and a potentiometer VR2. The potentiometer is adjusted to calibrate the circuit and to obtain the correct karat indication. The karat indication is obtained from meter M1, which is preliminarily set at 100% of full scale by adjusting potentiometer VR1. Diodes D1 and D2 provide a forward biased voltage drop of 0.7V each, and are coupled in parallel with the sample and in series with resistor R5. Meter M1 essentially reads the voltage on resistor R5, which is in parallel with resistor R4 and a portion of the resistance of potentiometer VR1—The adjustment of potentiometer VR1 increases or decreases the resistance in parallel with resistor R5. Potentiometer VR1 also changes the series resistance coupled to the meter, but the meter has a high input impedance, so this effect is not material. For example, the meter can be a Micronta model 22-221 or model 22-212B. Other meters are possible. Further loading is provided by resistor R6, in parallel with the sample. Millivoltmeter M2 can be used to set potentiometer VR2 to obtain the calibration setting needed. According to the resistance values shown in FIG. 6, the test circuit was calibrated as shown in Table I.

By testing reference samples of known purity, for example over a range of karat values from 8 to 18 karats, a table of voltages at millivoltmeter 17 can be developed, and the voltage reading thereafter obtained from an unknown sample can be compared with the reference values to determine the karat rating of the sample.

The tester effectively couples the drive battery 15 and the galvanic battery of the sample and probe, at reverse polarity. Thus, the drive battery stimulates the galvanic action at the sample. The EMF produced by the galvanic battery reduces the voltage across resistor R2, by an amount determined by the extent of galvanic action and by the resistance setting of potentiometer VR2. The voltage across resistor R2 is reduced to a greater extent where the sample is very different than the platinum of the probe (e.g., at low karat values), and to a lesser extent where the sample is more similar to platinum (e.g., at high karat values).

The particular electrolyte composition chosen can affect the sensitivity of the tester and the extent to which a mark is made at the site of contact between the probe and the sample. Dilute hydrochloric acid, for example a 4.0 to 8.0% solution, can be used as an electrolyte. However, this electrolyte does not always penetrate tarnished surfaces or surfaces that may be filmed over. A 1.0 to 4.0% solution of nitric acid can be added, which helps penetrate tarnish and eliminates the need for preliminary cleaning of the sample. A combination of nitric and hydrochloric acids is also possible.

TABLE I

| Calibration of VR2 | | | | 8 KT READINGS | | 10 KT READINGS | | 14 KT READINGS | | 18 KT READINGS | | 24 KT READINGS | |
|---|---|---|---|---|---|---|---|---|---|---|---|---|---|
| TURNS | OHMS | FULL SCALE | mV | METER % | mV | METER % | mV | METER % | mV | METER % | mV | METER % | mV |
| 0 | 0 | 48 | 1049 | 8 | 689 | 13 | 737 | 46 | 883 | 70 | 955 | 78 | 976 |
| 3 | 200 | 52 | 1070 | 9 | 702 | 17 | 766 | 47 | 892 | 72 | 975 | 82 | 1005 |
| 6 | 400 | 60 | 1120 | 12 | 737 | 19 | 776 | 48 | 931 | 72 | 1013 | 82 | 1048 |
| 7.5 | 500 | 66 | 1161 | 14 | 772 | 20 | 823 | 50 | 960 | 72 | 1057 | 82 | 1089 |
| 9 | 600 | 71 | 1178 | 14 | 769 | 23 | 836 | 52 | 976 | 72 | 1061 | 82 | 1101 |
| 12 | 800 | 84 | 1246 | 21 | 842 | 27 | 882 | 60 | 1055 | 72 | 1110 | 82 | 1145 |
| 15 | 1000 | 98 | 1320 | 30 | 935 | 42 | 1000 | 61 | 1164 | 78 | 1197 | 84 | 1238 |

An alternative embodiment of the meter circuit is shown in FIG. 7, wherein diodes D1 and D2 are members of a rectifier bridge, and in the diode leg the circuit is loaded only by potentiometer VR2 and resistor R4. No serial resistance is inserted with meter M1, which is coupled directly in series with the two diodes. This circuit has good sensitivity.

The alternative meter circuit of FIG. 8 has a 9V power supply, preferably also using a battery. Potentiometer VR1 is used to calibrate the circuit such that the open circuit probe produces a full scale reading on meter M1, which in this case does not have a separate control on the meter leg and therefore is less subject to calibration adjustments. However the circuit produces stable and repeatable results.

Having calibrated the tester, probe 1 is touched against the sample 10, which is in turn coupled to the positive terminal of battery 15 through switch 16. The sample and probe form a galvanic cell or a second battery. When placed in the circuit, this galvanic second battery reduces the voltage reading at the meter to an extent that depends on the extent of galvanic action, which is strongest when the sample metal is most dissimilar to the platinum electrode, pure gold being more similar to platinum than alloyed gold, which includes metals that are farther from platinum on the periodic table.

A preferred electrolyte comprises nitric and hydrochloric acids, and ammonium chloride. Ammonium chloride ($NH_4Cl$) is an ammonium salt of a relatively strong acid. As a salt, ammonium chloride is the combination of equivalent quantities of acid and base. It is readily soluble in water and accordingly dissociates in water to $NH_4^+$ and $Cl^-$, forming an electrolyte solution having electrical conductivity. If replacement is complete, the salt is normal. However, if replacement is not complete, then some hydrolysis may occur where either the $NH_4^+$ cation or the $Cl^-$ anion in solution combines with either an $OH^-$ anion or an $H^+$ cation from the water, respectively, leaving an excess amount of the other ion in solution. This makes the solution either slightly acidic or slightly basic due to hydrolysis.

Ammonium chloride will become acidic in aqueous solution due to hydrolysis and loss of $NH_4^+$ in solution. However, it provides additional free ions for carrying charge, and can increase the span of the test circuit and its sensitivity in distinguishing levels of gold purity. Ammonium chloride in a 10 to 15% solution can be used as the electrolyte, or preferably is combined with dilute nitric acid, which combination has been found to perform well in the tester of the invention and to improve the span (sensitivity)

of measurement by 25 to 30%. Table II represents a comparison of eight electrolyte formulations containing nitric acid, hydrochloric acid and/or ammonium chloride in a range of 0–4% nitric, 0–8% hydrochloric and 0–15% ammonium chloride, these ranges being the weight proportions used mixing 70% nitric acid solution by weight, with 38% hydrochloric acid solution by weight, and solid ammonium chloride salt by weight. The meter readings shown are percent of full scale after calibrating the circuit of FIG. 6 to 1,304 mV and a meter reading of 95% of full scale.

TABLE II

| ELECTROLYTE COMPOSITION | | | METER READINGS, % OF FULL SCALE | | | | | | |
|---|---|---|---|---|---|---|---|---|---|
| % $HNO_3$ | % HCL | % $HN_4Cl$ | 8 KT | 10 KT | 14 KT | 18 KT | 24 KT | Pd | Pt |
| 0 | 6 | 0 | 42–44 | 46–50 | 68–72 | 80 | 93 | 95–98 | 98 |
| 3 | 5 | 4 | 32 | 36 | 60 | 75 | 92 | 90–96 | 98 |
| 4 | 8 | 4 | 16 | 22 | 44 | 60 | 74 | 70–80 | 88 |
| 0 | 0 | 15 | 28 | 32 | 50 | 62 | 70 | 70–88 | 94 |
| 1 | 0 | 12 | 39 | 42 | 64 | 74 | 84 | 86–94 | 97 |
| 0 | 8 | 0 | 28–32 | 36–44 | 58–62 | 72–76 | 80–82 | 86–88 | 94 |
| 2 | 4 | 3 | 28 | 34 | 60 | 76 | 87 | 86–92 | 98 |
| 1 | 0 | 10 | 36 | 40 | 64 | 78 | 88 | 88–90 | 96 |

Figure 10:
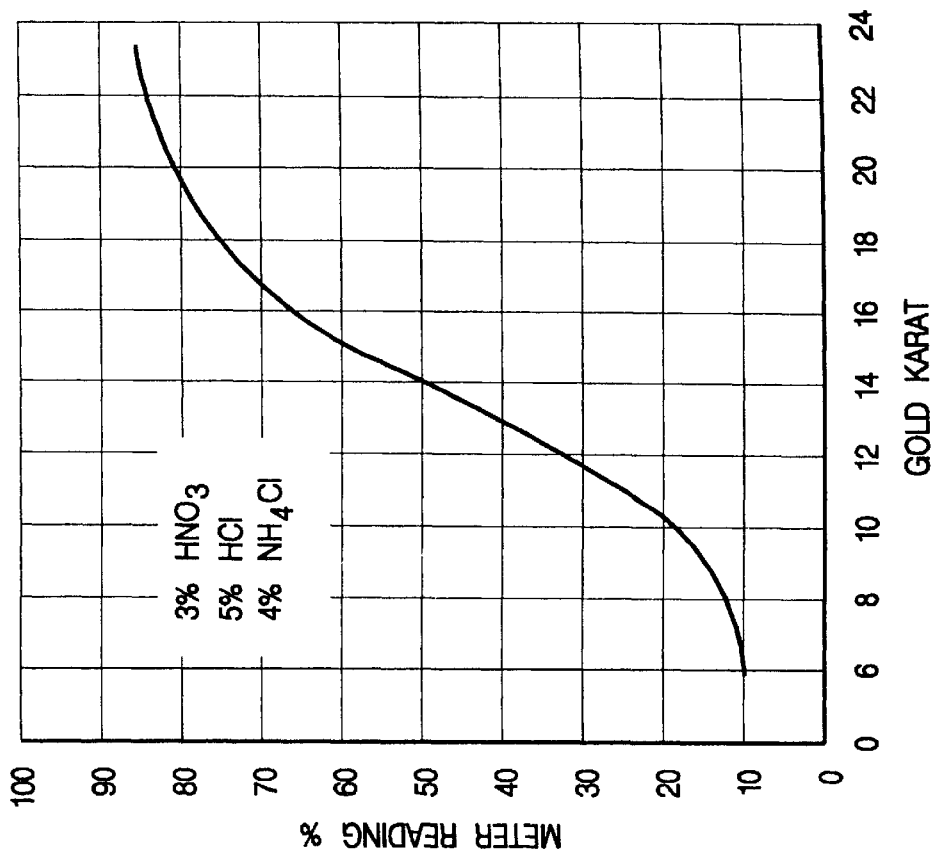
FIGS. 9 and 10 are graphs showing test results comparing meter readings as percent of full scale, for different electrolytes used in the probes and circuits of FIGS. 1–8.
Figure 9:
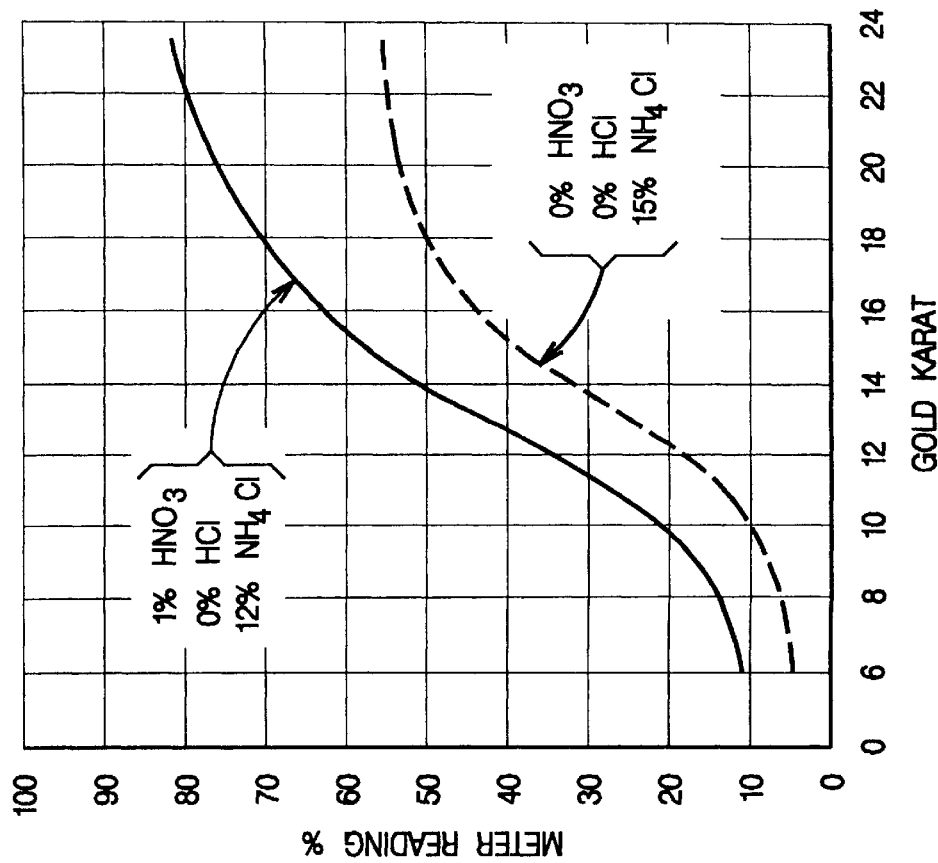

FIGS. 4–7 are graphs showing test results obtained using the apparatus and methods of the invention, and comparing the readings obtained for different electrolytes. The slope of the curve representing meter reading vs. karat value varies over the karat range. When testing samples believed to fall within a particular range of karat values, the electrolyte and potentiometer setting can be chosen to provide the greatest difference (i.e., the highest slope) in the range of interest. FIG. 9 compares meter readings over a range of karat value vs. meter reading for two electrolytes, namely a weak acid mix of 1%-0%-12% nitric, hydrochloric and ammonium chloride, and a substantially normal electrolyte of 15% ammonium chloride solution. These results suggest that the weak acid mix is preferable at high karat levels, but either solution produces an easily distinguished span over the range of 8–18 karats. FIG. 10 shows that a strong acid mix of 3%-5%-4% nitric, hydrochloric and ammonium chloride, produces a very good span of readings over 6–24 karats. However, as discussed above, a strong acid solution is more likely to mark the sample.

The millivolt readings obtained according to the circuit shown tend to rise over time if the tester remains connected to the sample, which is believed to be due to exhaustion of the available electrolyte at the sample. This effect is greater at low karat values than at high values, due to the greater galvanic action. For example, the reading obtained with a ten karat sample can rise several percent over one minute, while the reading for a 24 karat sample may rise only one percent. It is therefore appropriate to note the reading promptly after touching the probe to the sample. Whereas the probe of the invention is arranged to require no substantial preliminary steps of discharging electrolyte and the like, such quick readings are facilitated. The end of the probe can be cleaned when necessary (e.g., when testing gold after brass) by touching the tip to an absorbent material such as a paper towel or the like, and thereby to wick fresh electrolyte toward the surface.

It is advantageous when testing gold, for example, to touch the probe tip to the sample briefly two or three times, until the reading obtained is consistent (due to sufficient wetting of the probe tip. A brief touch is preferred due to potential decay of the electrolyte over time. For testing relatively pure platinum, a longer touch can be made without adversely affecting the reading obtained.

After a sample has been tested, capillary action quickly redistributes the electrolyte in the tip of the probe, enabling a further test after a short time period. This time period for recovery of the electrolyte is minimum where the probe is only briefly touched against the sample to obtain a reading, then withdrawn, because testing in this manner uses the least electrolyte in the galvanic reaction.

The probe of the invention is advantageously used to verify quickly the suspected karat values of samples, to screen samples for further testing and the like. In testing items of jewelry, it is possible using the probe to test for purity at different areas of the sample, such as areas adjacent a setting or at a solder joint, or the chain as well as the setting of a pendant. There is minimal damage to the sample, which typically can be cleaned with the mildest of abrasives (e.g., a pencil eraser) to remove all evidence of the test.

While a preferred embodiment of the present invention has been described and illustrated in the drawings, such description and illustration are by way of example, and it is to be understood that modifications could be made without departing from the scope or spirit of this invention.

I claim:
1. A method for analyzing a test specimen for metal content comprising:
   a. providing an electrolyte to a reservoir within a probe, said probe having an absorbent, non conductive, fiber tip and a non-conductive coating material surrounding the sides of the fiber tip leaving a limited portion of the end of the fiber tip free to contact the test specimen, said coating material defining a small, specific and repeatable area of actual contact between the fiber tip and the test specimen, and a metallic electrode in contact with the tip,
   b. saturating the fiber tip with the electrolyte,
   c. contacting a portion of the test specimen with the probe such that the area of contact between the fiber tip and the test specimen is small, specific and repeatable with respect to a test specimen,
   d. applying a substantially constant source of electromotive force between the electrode and the specimen,
   e. measuring a magnitude of an electromotive force generated by galvanic action between the electrode and a portion of the specimen contacted by the fiber probe tip, and
   f. comparing the magnitude obtained with the test specimen to magnitudes obtained from testing references of known metal content, to determine a relative metal content of the test specimen.

2. The method of claim 1, wherein said applying of a substantially constant source of electromotive force between the electrode and the specimen includes adjusting a voltage source to a predetermined value, coupling the voltage source to a galvanic cell formed by the electrode, the specimen and the electrolyte, such that the galvanic cell is at an opposite polarity from the voltage source.

3. The method of claim 2, further comprising adjusting a resistance in series with the voltage source and the galvanic cell, for adjusting a level of the magnitude obtained from the test specimen.

4. The method of claim 3 further comprising providing an electrolyte comprising an aqueous solution of acid and ammonium chloride.

5. The method of claim 3 further comprising providing an electrolyte comprising an aqueous solution by weight of about 3% nitric acid, about 5% hydrochloric acid and about 4% ammonium chloride.

6. The method of claim 3 further comprising providing an electrolyte comprising an aqueous solution of at least one of nitric acid, hydrochloric acid and ammonium chloride.

7. The method of claim 3 further comprising providing an electrolyte comprising an aqueous solution of ammonium chloride and at least one of nitric acid and hydrochloric acid.

8. The method of claim 3 further comprising providing an electrolyte comprising an aqueous solution of ammonium chloride.

9. The method of claim 3 further comprising providing an electrolyte comprising an aqueous solution of 12% ammonium chloride and 1% nitric acid.

10. The method of claim 3 further comprising providing an electrolyte comprising an aqueous solution of between 0–15% ammonium chloride, 0–4% nitric acid and 0–8% hydrochloric acid.

11. The method of claim 3 further comprising providing an electrolyte comprising a non-corrosive aqueous solution.

* * * * *